United States Patent [19]

Machida et al.

[11] Patent Number: 5,017,427

[45] Date of Patent: May 21, 1991

[54] LAMINATE HAVING INDICATOR FUNCTION

[75] Inventors: Morihisa Machida, Hayama; Yoshio Tajima, Ito; Hideo Nakatsumi, Ichikawa; Tatsuo Isahai, Takasaki; Daijiro Shiroki, Nagareyama, all of Japan

[73] Assignees: The Yokohama Rubber Co., Ltd.; Hitachi, Ltd., both of Tokyo, Japan

[21] Appl. No.: 243,559

[22] PCT Filed: Dec. 7, 1987

[86] PCT No.: PCT/JP87/00945

§ 371 Date: Aug. 5, 1988

§ 102(e) Date: Aug. 5, 1988

[87] PCT Pub. No.: WO88/04234

PCT Pub. Date: Jun. 16, 1988

[30] Foreign Application Priority Data

Dec. 8, 1986 [JP] Japan .................. 61-290530

[51] Int. Cl.$^5$ .................. B32B 5/16; A41D 19/00
[52] U.S. Cl. .................. 428/323; 428/518; 428/913; 2/168
[58] Field of Search .................. 428/323, 518, 913

[56] References Cited

U.S. PATENT DOCUMENTS

| | | | |
|---|---|---|---|
| 4,079,160 | 3/1978 | Phillipson | 428/217 |
| 4,425,161 | 1/1984 | Shibahashi et al. | 427/148 |
| 4,740,400 | 4/1988 | Lustig et al. | 428/518 |

*Primary Examiner*—P. C. Sluby
*Attorney, Agent, or Firm*—Armstrong, Nikaido, Marmelstein, Kubovcik & Murray

[57] ABSTRACT

A laminate comprising an inner layer containing an acid/base indicator and an outer layer containing no acid/base indicator, wherein the inner layer is capable of undergoing a color change upon its contact with an acid or an alkali.

7 Claims, No Drawings

LAMINATE HAVING INDICATOR FUNCTION

FIELD OF ART

The present invention relates to a laminate which includes an inner layer having the ability to change its color upon its contact with acid or alkali and which is in the form of, for example, working gloves.

BACKGROUND ART

In the manufacture of electronic parts and elements such as semi-conductor devices and so forth, a variety of chemicals such acids, alkalis, solvents and so forth are used in various treatment operations, starting with deburring of substrates and surface washing.

In carrying out such operations, conventionally it has been practice to make use of working gloves made of material of a laminate structure, comprising rubber or a resin having a rubber elasticity and a substantial resistance to chemicals. However, the treatment operations deal with strongly harmful chemicals such as strong acids and strong alkalis, so that penetration of chemical into the gloves contacted with the chemical, which can occur through any rupture in the glove material, tends to result in a serious accident. Therefore, measures are taken, for example such as to carry out an inspection to locate any breakage in the gloves by a pinhole finding test or to discard used gloves as waste after the lapse of the prescribed length of time of use of the gloves regardless of the possibility that the gloves can still be used.

In the above circumstances, it has been strongly desired in the art to develop such gloves having a laminate structure which have a high degree of safety and are economical.

The present invention has been made in order to obviate the above indicated problems in the art, and is directed in its object to provide a laminate which includes a layer capable of undergoing an internal color change in contact with an acid or an alkali (hereinafter referred to as a color indicator layer) and thereby provide the ability to detect permeation of acid or alkali into the laminate. According to the present invention, it is feasible to provide gloves having such a laminate structure containing a detecting function as above, which are relatively thin and can be used safely and, through the use of which, operations can be facilitated.

DISCLOSURE OF THE INVENTION

To attain the above object, the laminate having an indicator function according to the present invention is characterized by an inner layer and an outer layer, of which the inner layer contains a chemical acid/base indicator.

BEST MODE FOR CARRYING OUT THE INVENTION

Now, a detailed description will be given of the features constituting the present invention.

(1) Outer Layer:

Preferably, the outer layer should be transparent so that a color change of an underlying color indicator layer can be visually ascertained. In addition, the outer should have a resistance to acid and alkali. This outer layer does not necessarily comprise a single layer, but it may comprise a plurality of layers comprising different materials or having different characteristics, as need be.

Although no particular limitation is applied to the material for the outer layer, since this layer is subjected to a direct contact with an acid or an alkali, it is advantageous to make use of such materials as having a substantially resistant to acid and alkali. For example, chlorosulfonated polyethylene, chlorinated polyethylene and butyl rubber are suitably useful, but it is also feasible to use any other rubber or resin, as required.

(2) Inner Layer:

The inner layer, which lies next to the outer layer or outer layers as above, comprises a layer containing a chemical acid/base indicator, namely a color indicator layer which functions to present a color change upon its contact with any acid or an alkali which may migrate into this layer through any breakage in the outer layer or layers.

A chemical acid/base indicator of a suitable color changing characteristic (over a pH range) may be selected and employed for use, by considering the pH value of the particular acid or alkali with which the laminate is usually in contact. As examples of useful indicators phenolphthalein, methyl orange and congo red may be named. The amount of the indicator used in the inner layer must be such that the indicator presents a color change which can be detected, and it may be for example within a range of 0.5 to 1.5 parts by weight per 100 parts by weight of any suitable material, such as a rubber or resin which forms the color indicator layer.

The color indicator layer is not necessarily required to comprise a single layer but may comprise a plurality of layers. Where the color indicator layer comprises a plurality of layers, it is feasible to vary the chemical acid/base indicator between or among the layers.

As the principal material used for principal the color indicator layer, a suitable rubber or resin may be selectively employed.

Further, for example where the safety of the user is particularly required it may be suitable to provide next to, that is inner to, the color indicator layer, a further layer comprising a rubber or resin which is resistant to the contacted acid and alkali. In this case, it is feasible to effectively avoid the danger of exposure to the acid or alkali even if the color indicator layer is wholly destroyed.

The rubber or resin used for the color indicator layer and a further layer, which may possible be laminated next to, or inner to, the color indicator layer as need be is not limited to any particular one, and an appropriate may materially be selected for use dependent upon the conditions under which the laminate is used.

When necessary, further, components such as a crosslinking agent, a filler, a dispersing agent and so forth, may be blended in with the rubber or resin used for the outer layer and any of the other layer or layers.

Examples will be shown below.

EXAMPLES

Nitrile rubber (a latex was used and a crosslinking agent was added), was blended with various acid/base indicators as shown in Table 1 below, and the resulting mixture was dried and solidified to provide films useful as the color indicator layers, on which a film of chlorosulfonated polyethylene (a latex was used and a crosslinking agent was added) was formed. The resulting laminates were subjected to a heat-treatment at 140° C. for 30 minutes to obtain sheets of a two-layer structure. Then, an incision of a depth reaching the color indicator layer was applied to each sheet and an acid solution was applied dropwise at the location of the incision to determine the characteristic and the speed of changing of colors as a result of the contact of the color indicator layer with the acid, and the visibility of the color change through the outer layer.

Table 1 below also shows the results of the determinations made.

TABLE 1

| Outer Layer | Chlorosulfonated Polyethylene | | | | | |
|---|---|---|---|---|---|---|
| Color Indicator Layer | Acrylonitrile-Butadiene Rubber Latex | | | | | |
| Acid/base Indicator | Methyl Orange | | | Congo Red | | |
| Acid | Sulfuric Acid | Nitric Acid | Hydrochloric Acid | Sulfuric Acid | Nitric Acid | Hydrochloric Acid |
| Colour Change | | | | | | |
| Before contact with acid | Orange | Orange | Orange | Red | Red | Red |
| After contact with acid | Red | Red | Red | Violet | Violet | Violet |
| Colour Change Speed | immediately changed from orange to pale red, and then to clear red | | | immediately changed from red to violet | | |
| Visibility | Good | Good | Good | Good | Good | Good |

As seen from the above Table 1, the color indicator layer containing methyl orange or congo red, suitable acid/base indicators, underwent a clear color change upon its contact with each of sulfuric acid, nitric acid and hydrochloric acid, and also the visibility of the color change through the outer layer was satisfactory, the colour change being fully ascertainable visually.

CAPABILITY OF EXPLOITATION OF THE INVENTION IN INDUSTRY

As stated above, according to the present invention a color indicator layer is provided in a laminate and thereby it is feasible to attain the following effects/results.

(1) With the laminate according to the invention, a layer provided next to, or inner to, an outer layer, having suitable chemical resistance, is imparted with the ability to change color upon its contact with an acid or an alkali, so that penetration of an acid or alkali through a breakage in the outer layer can be visually detected, whereby the safety in operations can be greatly enhanced.

(2) Since it can be perceived as a change in color, the generation of any breakage in the laminate can be detected with ease and without fail, so that it is feasible to manufacture gloves of a reduced thickness in comparison to conventionally produced gloves, whereby with use of the gloves made of a laminate according to the invention, various operations can be more easily performed.

(3) The degree of damage to the laminate can be told by the degree of a color change in or of the color indicator layer, so that an economical advantage can be brought about in that the need in the prior art, of having to discard gloves as waste after the lapse of the prescribed length of use time regardless of the possibility that the gloves can still stand the use in actuality is not longer necessary.

(4) Also attributable to the above fact that the degree of a damage in the laminate can be told by the degree of a color change in the color indicator layer, an economization can be realized of the time and the cost required for an inspection in that the conventionally indispensable pinhole finding tests can now be done away with.

(5) The laminate according to the present invention has a wide range of utility in addition to its application to gloves, for various goods such as a lining material, a covering material for machines and implements and so forth.

We claim:

1. A laminate, having a function of an indicator, comprising a rubber or resin inner layer which contains an acid/base indicator which changes color upon contact with an acid or an alkali; and an acid or alkali resistant outer layer.

2. A laminate as claimed in claim 1, wherein said outer layer is transparent.

3. A laminate as claimed in claim 1, wherein said outer layer comprises at lease one of chlorosulfonated polyethylene, chlorinated polyethylene or butyl rubber.

4. A laminate as claimed in claim 1, wherein said acid/base indicator is phenolphthalein, methyl orange or Congo red.

5. A laminate as claimed in claim 1, wherein said inner layer comprises an acid or base resistant rubber or a resin.

6. A laminate as claimed in claim 1, wherein said inner layer comprises a plurality of layers each containing a different acid/base indicator.

7. A laminate comprising a transparent outer layer; inner layer, each comprising a substantially acid or alkali resistant material; and an intermediate layer containing an acid or alkali indicator which changes color upon contact with an acid or an alkali.

* * * * *